United States Patent [19]

Rodewald

[11] 3,962,133

[45] June 8, 1976

[54] GRAPHITE INTERCALATION

[75] Inventor: Paul G. Rodewald, Rocky Hill, N.J.

[73] Assignee: Mobil Oil Corporation, New York, N.Y.

[22] Filed: Dec. 12, 1974

[21] Appl. No.: 532,146

[52] U.S. Cl.............................. 252/433; 252/429 R; 252/437; 252/439; 252/441; 252/447; 208/114; 208/115; 260/683.66; 260/683.68; 260/683.15 A; 260/671 C; 260/683 D
[51] Int. Cl.².......................................... B01J 27/12
[58] Field of Search ........... 252/433, 437, 441, 447, 252/439, 429 R

[56] References Cited
UNITED STATES PATENTS

| 3,756,962 | 9/1973 | Brinker et al...................... 252/441 |
| 3,763,043 | 10/1973 | Thompson ....................... 252/439 X |
| 3,785,999 | 1/1974 | Derleth et al....................... 252/441 |
| 3,804,916 | 4/1974 | Lalanchette ..................... 252/447 X |
| 3,835,067 | 9/1974 | Schneider ........................... 252/447 |
| 3,840,566 | 10/1974 | Lalanchette ..................... 252/447 X |
| 3,847,963 | 11/1974 | Lalanchette ..................... 252/447 X |

*Primary Examiner*—Patrick P. Garvin
*Attorney, Agent, or Firm*—Charles A. Huggett; Raymond W. Barclay

[57] ABSTRACT

Intercalation of a Lewis acid fluoride in graphite is effected in the presence of gaseous fluorine. The reaction results in new compositions useful as catalysts and as atmospheric pressure containers for normally gaseous Lewis acid fluorides.

12 Claims, No Drawings

GRAPHITE INTERCALATION

BACKGROUND OF THE INVENTION

1. Field of the Invention

This invention relates to the intercalation of a Lewis acid fluoride in graphite giving rise to products useful in catalysis and as atmospheric pressure storage for normally gaseous Lewis acid fluorides.

2. Description of the Prior Art

The intercalation of various salts in the lattice of graphite has previously been described. Thus, it has been reported in J. Chem. Soc., Chem. Comm., 21, 815 (1973) that while there have been few instances of intercalation of fluorides in graphite, the intercalation of antimony pentafluoride in the lattice of graphite is accomplished by heating a mixture of $SbF_5$ and graphite at 110°C for a few days. It has also been known to accomplish the conversion of hydrocarbons in the presence of a wide variety of catalysts including those in which the active catalytic component is deposited on a porous inert support such as, for example, graphite. U.S. Pat. No. 3,678,120 describes such process in which the catalyst employed is a porous inert solid support having deposited thereon a catalytic complex of an antimony pentafluoride component and a hydrogen fluoride or a fluorosulfonic acid component. It has been reported in U.S. Pat. No. 3,708,553 that hydrocarbon conversion and more specifically alkylation can be carried out in the presence of a Lewis acid such as antimony pentafluoride combined with a Bronsted acid such as fluorosulfuric acid. In none of this prior art, which is the most relevant known, is there any recognition or disclosure of intercalating a Lewis acid fluoride in graphite in the presence of gaseous fluorine, nor is there any disclosure of intercalates of boron trifluoride or phosphorus pentafluoride with the graphite.

SUMMARY OF THE INVENTION

In accordance with the present invention, there is provided a method for manufacturing intercalates of a Lewis acid fluoride with graphite not heretofore available. Such method entails effecting intercalation in the presence of fluorine which appears to act as a catalyst for the reaction and is not retained in the graphite structure.

It has been found that the new method affords means for the production of novel compositions of certain Lewis acids, notably boron trifluoride and phosphorus pentafluoride, which have not previously been capable of intercalation in graphite.

Thus, it has been observed that when $BF_3$ or $PF_5$ are streamed through a bed of graphite, no intercalation occurs. Similarly, when fluorine, diluted with nitrogen to yield a mixture of 10 volume percent fluorine is streamed through a bed of graphite, no intercalation occurs. However, when the above Lewis acid fluorides are costreamed with fluorine diluted with nitrogen to the indicated concentration, rapid intercalation of the Lewis acid fluoride occurs.

The present process comprises contact of graphite with a Lewis acid fluoride, having a boiling point below about 300°C and preferably below about 150°C, in the presence of fluorine at a temperature within the approximate range of −20°C to 300°C for at least a period of time to effect a weight increase in the graphite. Generally, the reaction is carried out at approximately atmospheric pressure, although the pressure may be within the range of about 1 to about 10 atmospheres. The reaction temperature desirably is between about 15°C and about 150°C and preferably between about 20°C and about 40°C. The time of contact is such as to introduce the desired amount of Lewis acid fluoride into the graphite and generally is between about ¼ and about 24 hours and more usually between about 1 and about 10 hours.

It is essential in accordance with the present method that contact of the graphite and Lewis acid fluoride takes place in the presence of fluorine. Individual streams of the Lewis acid fluoride and fluorine may be simultaneously brought into contact with the graphite under the above conditions. A particularly feasible means for contacting the reactants involves prior admixing of the Lewis acid fluoride and fluorine and thereafter contacting the graphite with such mixed stream. The relative amounts of Lewis acid fluoride and fluorine employed, on a weight basis are generally between about 30:1 and about 2:1. Fluorine may be used in undiluted form, but it is generally preferred to dilute the fluorine with an inert gas, e.g. nitrogen, helium or argon, such that the fluorine stream contains, on a volume basis, between about 1 and about 50 percent fluorine.

After completion of the reaction, an inert gas such as nitrogen, helium or argon is desirably passed through the bed of graphite containing intercalated Lewis acid fluoride at a sufficient rate and for a sufficient time to sweep fluorine and any non-intercalated Lewis acid fluoride from the pores of the graphite. The intercalated product so obtained generally contains between about 5 and about 50 weight percent and preferably between about 10 and about 40 weight percent of Lewis acid fluoride. The density of the intercalate is substantially less than that of the starting graphite, attributable to a considerable degree of expansion in the final product.

The Lewis acid fluoride intercalated in graphite in accordance with the present invention is generally one having the formula $MX_n$ where M is an element selected from Group II, IIIA, IV, V or VI-B of the Periodic Table, X is fluorine or fluorine in combination with oxygen and n is an integer of from 2 to 5. Representative of such compounds are vanadium pentafluoride, boron trifluoride, niobium pentafluoride, tantalum pentafluoride, silicon tetrafluoride, germanium tetrafluoride, selenium tetrafluoride, antimony pentafluoride, tellurium tetrafluoride, sulfur tetrafluoride, bismuth pentafluoride, molybdenum pentafluoride, iodine pentafluoride, bromine pentafluoride, phosphorus pentafluoride, and arsenic pentafluoride. In addition to the fluorides, oxyfluorides of the transition metals, e.g. chromium oxyfluoride, are particularly preferred embodiments of the latter type compounds. The Lewis acid fluorides, characterized by a boiling point below about 300°C and preferably below about 150°C, may be employed as such or generated in situ by the reaction of any salt capable of being oxidized by fluorine to fluorides. Thus, it is contemplated that a salt of a metal, which forms a Lewis acid fluoride boiling below about 300°C, such as a suitable metal chloride, bromide or iodide, may be initially used in the intercalation reaction conducted, in accordance with the present invention, in the presence of fluorine and during such reaction the Lewis acid fluoride will be formed in situ by reason of the interaction of such salt, e.g. chloride, bromide or iodide and fluorine.

Intercalation of some of these Lewis acid fluorides with graphite, e.g. antimony pentafluoride, has previously been achieved utilizing a method other than that described herein. Other of the Lewis acids, e.g. boron trifluoride and phosphorus pentafluoride, have not been capable of production by previously known techniques and are considered to be new compositions useful as catalysts in conversion of organic compounds including, by way of example, isomerization, polymerization, cracking and alkylation.

In one embodiment of the invention, the graphite/intercalated Lewis acid composite catalyst may additionally have intercalated in the graphite a Bronsted acid such as hydrofluoric acid, hydrochloric acid, fluorosulfuric acid or trifluoromethane-sulfonic acid and mixtures thereof. In another embodiment of the invention, the graphite/intercalated Lewis acid fluoride composite may have a Group VI-B or Group VIII metal additionally intercalated in the graphite to provide a highly effective catalyst.

The graphite utilized in the present invention is desirably characterized by a surface area of about 0.3 to about 50 m$^2$/gram; a typical graphite applicable for use in the present invention is characterized by the following properties:

Surface Area of 0.46 m$^2$/gram
Real Density of 2.16 gram/cc
Particle Density of 1.90 gram/cc
Pore Volume of 0.065 cc/gram When a Bronsted acid, such as hydrofluoric acid, hydrochloric acid, fluorosulfuric acid or trifluoromethanesulfonic acid is also intercalated in the graphite lattice, the amount thereof is generally between about 0.5 and about 75 weight percent and preferably between about 1 and about 50 weight percent, with the molar ratio of Bronsted to Lewis acid fluoride being within the range of .1:1 to 50:1 and more particularly in the range of 1:1 to 5:1.

When a Group VI-B or Group VIII metal is additionally intercalated in the graphite, the amount employed is such as to afford a resulting composite containing between about 0.1 and about 20 weight percent of the metal. With metals of the platinum group, the amount of metal is preferably in the approximate range of 0.1 and 5 weight percent. Other metals contemplated for intercalation include nickel, cobalt, iron chromium, molybdenum and tungsten. Particularly preferred are the Group VIII metals, especially platinum and palladium.

When a metal of Group VI-B or Group VIII is also desired in the catalyst, intercalation is achieved by heating a compound of the appropriate metal with graphite, preferably in the presence of chlorine, at a temperature within the approximate range of 100° to 200°C for a period of between about 4 and about 24 hours. The intercalated metal compound is then reduced, generally with flowing hydrogen, at a temperature of about 300° to about 400°C for a period of approximately 8 to 24 hours. Thereafter, intercalation of the desired Lewis acid fluoride into the metal/intercalated graphite composite may be effected as described above.

In similar fashion, when a Bronsted acid is additionally desired in the catalyst, such acid may be intercalated after intercalation of the Lewis acid fluoride into the lattice of the graphite. Intercalation of the Bronsted acid is achieved by heating the graphite with such acid at a temperature between about −40°C and about 100°C for a period of between about 1 and about 5 hours. It is also feasible and, in some instances preferable, to intercalate both (1) a metal of Group VI-B or Group VIII and (2) a Bronsted acid into the lattice of the graphite having Lewis acid fluoride under the conditions specified hereinabove, and then intercalation of the Bronsted acid as described.

A wide variety of hydrocarbon conversion reactions may be effected utilizing the present catalyst. Such conversion processes include those catalyzed by the presence of acidic sites such as cracking, isomerization, alkylation, polymerization, disproportionation, dealkylation, transalkylation and similar related processes. These processes are effected by contacting a hydrocarbon or hydrocarbon mixture with the above-described catalyst at hydrocarbon conversion conditions. The catalyst to hydrocarbon weight ratio employed is generally between about 1:5 and about 1:20. The temperature employed is generally between about 0°C and about 650°C. Contact between the catalyst and hydrocarbon charge may take place utilizing any of the conventional systems such as a fixed bed system, a moving bed system, a fluidized bed system or a continuous or batch-type operation. The hydrocarbon conversion utilizing the present catalyst may be carried out as either a vapor phase, a liquid phase or a mixed phase operation. Conversion may take place in the absence or presence of hydrogen. Operation in the presence of hydrogen is particularly advantageous for isomerization in preserving catalyst life.

Isomerization of isomerizable hydrocarbons, such as naphthenes and/or paraffins, may be effectively carried out utilizing the catalyst of this invention. Thus, isomerization of straight chain or slightly branched chain paraffins containing 4 or more carbon atoms per molecule, such as normal butane, normal pentane, normal hexane, normal heptane, and normal octane may be readily effected. Likewise, cycloparaffins containing at least 5 carbon atoms in the ring, such as alkyl cyclopentanes and cyclohexanes may be effectively isomerized utilizing the present catalyst. It is contemplated that straight or branched chain saturated hydrocarbons containing up to 30 carbon atoms or more per molecule may be isomerized with the present catalyst, regardless of the source of such hydrocarbons or mixtures containing the same. As examples of commercial mixtures, mention can be made of straight-run tops or light naphtha fractions which in various refineries are available in large amounts.

In carrying out isomerization of isomerizable hydrocarbons utilizing the present catalyst, contact between the catalyst and hydrocarbon charge is conducted at a temperature between about 0°C and about 200°C and preferably between about 30°C and about 150°C at a pressure between about atmospheric and about 30 atmospheres or more. The hydrocarbon charge is passed over the catalyst at a liquid hourly space velocity generally between about 0.2 and about 10 and preferably between about 0.5 and about 4. The resulting product is withdrawn from the reaction zone, separated from the reactor effluent and recovered by any suitable means such as fractional distillation. Any unreacted starting material may be recycled to form a portion of the feedstock.

The catalyst of this invention is also suitable for catalyzing hydrocarbon cracking. The hydrocarbon charge in such process may comprise one or more normal paraffins or may be a complex mixture of paraffins, naphthenes and aromatics, such as occurs in petroleum gas oil, which is the feedstock normally conducted to a commercial catalytic cracking unit. Hydrocarbon cracking utilizing the catalyst of this invention is essentially conducted at a temperature between about 400°C and 650°C, a pressure of from about atmospheric to about 5 atmospheres and employing a liquid hourly space velocity of between about 0.5 and about 100.

Alkylation employing the catalyst described herein may also be effectively carried out. Thus, alkylation of an alkylatable hydrocarbon with an olefin, alkyl halide or alcohol is desirably effected in the presence of the catalyst of this invention at alkylation conditions including a temperature of about 0°C to about 150°C and a pressure of between about atmospheric and about 500 psig. The mole ratio of alkylatable hydrocarbon to alkylating agent is preferably between about 1:1 to about 10:1.

Polymerization of polymerizable organic compounds, such as olefins and tetrahydrofuran may be effectively conducted in the presence of the catalysts described herein. Such polymerization is suitably effected at a temperature between about $-20°C$ and about 100°C and preferably between about 0°C and about 50°C at a pressure between about atmospheric and about 10 atmospheres utilizing a batch or container operation. The charge is passed over the catalyst at a liquid hourly space velocity generally between about 0.5 and about 1000 and preferably between about 1 and about 200.

In addition to use as catalysts, the intercalates of the lower boiling Lewis acid fluorides with graphite afford atmospheric pressure storage for the normally gaseous Lewis acid fluorides. It is contemplated that Lewis acid fluorides having a boiling point less than about 50°C may be employed for such purpose. Thus, although both $BF_3$ and $PF_5$ are low boiling compounds, having boiling points of $-99°C$ and $-75°C$ respectively, the graphite intercalates have been observed to degas quite slowly at ambient temperature. Thermogravimetric analysis has shown that gas evolution becomes rapid at 100°–200°C. These intercalates are thus useful as atmospheric pressure containers for $BF_3$ or $PF_5$. The need for high pressure equipment is obviated. A known amount of gas could be generated by heating the corresponding weight of intercalate. For example, heating 10 grams $BF_3$/graphite intercalate (21.2 weight percent $BF_3$) to 150°C would generate 2.12 grams or 700 cc of $BF_3$.

DESCRIPTION OF SPECIFIC EMBODIMENTS

The following examples will serve to illustrate the invention without limiting the same:

EXAMPLE 1

Intercalation of $BF_3$ in graphite was accomplished by costreaming $BF_3$ and 10 weight percent fluorine in nitrogen each at 40 cc/minute through a 10 gram bed of graphite.

The bed temperature increased rapidly from 22°C to 34°C and then gradually decreased to 24°C over a 90 minute contact time. Dry nitrogen was then passed through the bed for 30 minutes at 80 cc/minute. No $BF_3$ fumes were evident in the off gas.

The weight increase of the graphite was 1.91 grams, corresponding to a 16 weight percent $BF_3$ loading. The density of the graphite decreased from 0.845 gram/cc to 0.573 gram/cc, corresponding to a 76 percent volume expansion. X-ray diffraction analysis indicated that the intercalate is third stage (every third layer occupied by $BF_3$) and that the layer spacing for graphite increased from 3.35A. to 7.60A. The elemental analysis in weight percent was

|   | Theory | Observed |
|---|--------|----------|
| B | 2.58   | 2.56     |
| F | 13.62  | 13.06    |

EXAMPLE 2

Intercalation of $PF_5$ in graphite was accomplished by costreaming $PF_5$ and 10 volume percent of fluorine in nitrogen each at 40 cc/minute through a 15 gram bed of graphite.

The bed temperature increased rapidly from 23°C to 39°C and then gradually dropped to 24°C over a 120 minute contact time. Dry nitrogen was then passed up through the bed for 25 minutes at 80 cc/minute. No $PF_5$ fumes were evident in the off gas.

The weight increase of the graphite was 5.37 grams, corresponding to a 26.4 weight percent $PF_5$ loading. The density of the graphite decreased from 0.845 gram/cc to 0.57 gram/cc, corresponding to a 101% by volume expansion. X-ray diffraction analysis indicated that the $PF_5$ intercalate is third stage (every third layer occupied by $PF_5$) and that the layer spacing for graphite increased from 3.35A. to 7.60A.

EXAMPLE 3

To a 125 cc flask was added 10.00 grams graphite and 7.40 grams $SbF_5$ under a nitrogen atmosphere. Ten percent fluorine/nitrogen mixture was passed through the flask at 54 cc/minute. After stirring for 10 minutes the product became free flowing and had a lustrous blue-black appearance. Upon exposure of the intercalate to air, no fuming occurred. The density of the product was 0.833 g/cc compared to 0.845 g/cc for the starting graphite. Elemental analysis showed the mole ratio of F to Sb to be 4.97, in close agreement to the theoretical ratio of 5.00.

EXAMPLE 4

This example was carried out in the absence of fluorine and serves to show the advantage of the presence of this gas. To a 125 cc flask was added 10.57 grams graphite and 7.82 grams $SbF_5$ under a nitrogen atmosphere. After stirring for 19 hours the $SbF_5$ had not completely intercalated as evidenced by copious fuming of the product upon exposure to air. The product was free flowing and had a dull black appearance. The density of the product was 0.877 g/cc compared to 0.845 g/cc for the starting graphite.

The above two examples illustrate the improvement to be obtained by using fluorine as a catalyst for the intercalation of $SbF_5$ in graphite. In contrast to the previously employed technique, the intercalation time is reduced from more than one day to 30 minutes or less at room temperature and the temperature of intercalation is reduced from 110°C to room temperature.

EXAMPLE 5

To a 125cc flask was added 50cc tetrahydrofuran and $PF_5$/graphite (1.00g, 2.09 meq) intercalate prepared as in Example 2. The mixture was maintained at room temperature under nitrogen and was stirred. After one hour the mixture was difficult to stir. Upon standing overnight the tetrahydrofuran polymerized to a rigid glass.

EXAMPLE 6

Propylene was passed at 76 cc/min into a reactor containing 30 cc benzene and 1.00 gram $BF_3$/graphite (2.26 meq $BF_3$) intercalate, prepared as in Example 1. The reactor was fitted with a condenser and maintained at 70°C. The appearance of isopropylbenzene product was followed by gas chromatography. After two hours one mole isopropylbenzene/mole $BF_3$ had formed.

EXAMPLE 7

In a qualitative test isopropylchloride was observed to alkylate benzene at 70°C over the $BF_3$/graphite intercalate prepared as in Example 1. The isopropylbenzene product was observed by gas chromatography.

EXAMPLE 8

To a 200 cc flask was added 70.0 cc n-hexane containing 2.32 gram dissolved isobutene. The flask was swept out with dry nitrogen, placed in a bath thermostatted at 20°C and stirred. After 10 minutes the $BF_3$/graphite (2.00 g, 6.26 meq $BF_3$) intercalate prepared as in Example 1 was added. The ensuing rapid reaction was followed by gas chromatography. After 5 minutes, 98 percent of the isobutene had been converted to oligomers. Over the next seven hours small changes occurred in the oligomer distribution. The following table summarizes the oligomer distribution at two specified times.

| Reaction Time | Isobutene Conversion % | Dimer | Trimer | Tetramer | Pentamer | Hexamer | Heptamer | Octamer |
|---|---|---|---|---|---|---|---|---|
| 15 min | 98 | 7.9 | 37.3 | 26.3 | 14.7 | 9.0 | 4.7 | 0.0 |
| 7 hrs | 99 | 5.7 | 42.4 | 21.4 | 11.0 | 7.7 | 3.3 | 8.4 |

Oligomer Distribution (%)

The gas chromatograph also showed a small broad peak corresponding to nonamer. The oligomer groups were well separated and resolved into isomeric components. Further addition of 5.98 grams isobutene to the reaction mixture resulted in rapid conversion to oligomers having a similar distribution.

EXAMPLE 9

To a 200 cc flask was added 70.0 cc n-hexane containing 2.32 grams dissolved isobutene. The flask was swept out with dry nitrogen, placed in a bath thermostatted at 20°C and stirred. After 10 minutes the $PF_5$/graphite (3.00 g, 6.27 meq $PF_5$) intercalate prepared as in Example 2 was added. The ensuing reaction was rapid and was followed by gas chromatography. The following table summarizes the oligomer distribution at two specified times:

Oligomer Distribution (%)

| Reaction Time | Isobutene Conversion % | Dimer | Trimer | Tetramer | Pentamer | Hexamer | Heptamer | Octamer |
|---|---|---|---|---|---|---|---|---|
| 15 min | 45 | 21.7 | 28.3 | 21.1 | 14.2 | 8.7 | 6.0 | Trace |
| 7 hrs | 97 | 26.2 | 35.5 | 19.7 | 10.7 | 6.6 | 1.5 | Trace |

It is to be noted that the present dimer for the $PF_5$/graphite catalyzed reaction is considerably higher than that obtained from the $BF_3$/graphite reaction.

EXAMPLE 10

To a 200 cc flask was added 70.0 cc benzene and 3.15 grams (0.0414 mole) of t-butyl fluoride. The flask was swept out with dry nitrogen, placed in a bath thermostatted at 20°C and stirred. After 10 minutes the $BF_3$/graphite (2.00g 6.26 meq $BF_3$) intercalate, prepared as in Example 1, was added. A rapid reaction ensued and was monitored by gas chromatography. After 5 minutes the t-butyl fluoride peak had disappeared indicating 100 percent conversion to products. The product distribution is summarized in the following table:

| Reaction Time (min) | t-Butyl Fluoride Conversion (%) | t-Butyl-benzene | 1,3-Di-t-butylbenzene | 1,4-Di-t-butylbenzene |
|---|---|---|---|---|
| 5 | 100 | 73.6 | 3.7 | 22.7 |
| 60 | 100 | 74.0 | 3.7 | 22.3 |

EXAMPLE 11

To a 200 cc flask was added 70.0 cc benzene and 3.15 grams (0.0414 mole) t-butyl fluoride. The flask was swept with dry nitrogen, placed in a bath thermostatted at 20°C, and stirred. After 10 minutes the $PF_5$/graphite (3.00g, 6.27 meq $PF_5$) intercalate, prepared as in Example 2, was added. This alkylation took place more slowly than the $BF_3$/graphite catalyzed alkylation. Gas chromatographic analysis indicated a 54 percent conversion at one hour reaction time to a product comprising 70.4 percent t-butylbenzene, 1.9 percent 1,3-di-t-butylbenzene, and 27.8 percent 1,4-di-t-butylbenzene.

EXAMPLE 12

To a reactor maintained under nitrogen was added 99.5% n-hexane (6.0cc, 4.0g), $BF_3$/graphite (1.0cc, 0.44g, 1.2 meq $BF_3$) intercalate prepared as in Example 1 and fluorosulfuric acid (0.68g, 6.80 meq). The reactor was agitated and maintained at 22°C. Samples were withdrawn periodically for analysis by gas chromatography. The following table summarizes the product distribution after six hours (effective LHSV = 1). The n-hexane conversion at this point was 6%.

| Product Distribution | |
|---|---|
| Hydrocarbon | Wt. % |
| Propane | 0.8 |
| 2-Methylpropane | 24.0 |
| Butane | 0.8 |
| 2-Methylbutane | 25.0 |
| Pentane | 0.9 |
| 2,2-Dimethylbutane | 2.1 |
| 2,3-Dimethylbutane and 2-Methylpentane | 25.9 |
| 3-Methylpentane | 8.1 |
| $C_7^+$ | 12.4 |

The above results illustrate isomerization/disproportionation of n-hexane over $BF_3$/$HSO_3$/graphite catalyst.

EXAMPLE 13

This example illustrates that in contrast to fluorine, chlorine failed to catalyze the intercalation of $BF_3$ in graphite.

Boron trifluoride and 10 volume percent chlorine in nitrogen were costreamed each at 40 cc/min through a 15.00 g bed of graphite at 22°C. No temperature change was observed in the bed. After 3 hours contact time no intercalation had occurred as evidenced by no increase in weight of the graphite.

When $BF_3$, $PF_5$ or 10 volume percent fluorine in nitrogen were individually streamed through a bed of graphite (20–65 mesh), no intercalation occurred as indicated by no increase in weight of the graphite. The following table summarizes the data:

| Reactant | Flow Rate (cc/min.) | Contact Time (min.) | Temp. °C | Wt. of Graphite (grams) | Weight Increase |
|---|---|---|---|---|---|
| $BF_3$ | 40 | 90 | 22 | 10 | None |
| $PF_5$ | 40 | 100 | 24 | 20 | None |
| 10% F/$N_2$ | 40 | 255 | 24 | 20 | None |

It is to be understood that the foregoing description is merely illustrative of preferred embodiments of the invention of which many variations may be made by those skilled in the art within the scope of the following claims without departing from the spirit thereof.

I claim:

1. A method of intercalating a Lewis acid fluoride in graphite which comprises contacting graphite with a Lewis acid fluoride, having a boiling point below about 300°C., of an element of Group II, IIIA, IV, V or VIB of the Periodic Table in the presence of fluorine at a temperature within the approximate range of 15° to 150°C for at least a period of time to effect a weight increase in the graphite, the relative amount of said Lewis acid fluoride and fluorine being between about 30 to 1 and about 2 to 1 on a weight basis.

2. The method of claim 1 wherein the temperature is between about 20°C and about 40°C.

3. The method of claim 1 wherein the Lewis acid fluoride is boron trifluoride.

4. The method of claim 1 wherein the Lewis acid fluoride is phosphorus pentafluoride.

5. The method of claim 1 wherein the Lewis acid fluoride is antimony pentafluoride.

6. The method of claim 1 wherein said period of time is between about ¼ and about 24 hours.

7. The method of claim 1 wherein said period of time is between about 1 and about 10 hours.

8. The method of claim 1 wherein the fluorine is diluted with an inert gas such that the fluorine content of the diluted mixture is between about 1 and about 50 volume percent.

9. A composition consisting essentially of graphite having intercalated in the lattice thereof between about 5 and about 50 weight percent of boron trifluoride.

10. A composition consisting essentially of graphite having intercalated in the lattice thereof between about 5 and about 50 weight percent of phosphorus pentafluoride.

11. The composition of claim 9 wherein the intercalated amount of boron trifluoride is between about 10 and about 40 weight percent.

12. The composition of claim 10 wherein the intercalated amount of phosphorus pentafluoride is between about 10 and about 40.

* * * * *

UNITED STATES PATENT AND TRADEMARK OFFICE
CERTIFICATE OF CORRECTION

PATENT NO. : 3,962,133
DATED : June 8, 1976
INVENTOR(S) : PAUL G. RODEWALD

It is certified that error appears in the above-identified patent and that said Letters Patent are hereby corrected as shown below:

Column 6, line 9, "E" should be --F--.

Signed and Sealed this

Eighth Day of March 1977

[SEAL]

Attest:

RUTH C. MASON
*Attesting Officer*

C. MARSHALL DANN
*Commissioner of Patents and Trademarks*